United States Patent

Tanji et al.

[11] Patent Number: 5,304,159
[45] Date of Patent: Apr. 19, 1994

[54] DISPOSABLE DIAPERS

[75] Inventors: Hiroyuki Tanji; Ichiro Wada; Yoshio Ono; Hiroyuki Soga, all of Kawanoe, Japan

[73] Assignee: Uni-Charm Corporation, Ehime, Japan

[21] Appl. No.: 43,751

[22] Filed: Apr. 7, 1993

[30] Foreign Application Priority Data

Apr. 21, 1992 [JP] Japan .................. 4-101340

[51] Int. Cl.$^5$ .................................................. A61F 13/15
[52] U.S. Cl. ................................... 604/385.2; 604/358
[58] Field of Search ............... 604/358, 385.1, 385.2

[56] References Cited

U.S. PATENT DOCUMENTS

| 5,080,658 | 1/1992 | Igaue et al. | 604/385.2 |
| 5,167,653 | 12/1992 | Igaue et al. | 604/385.2 |
| 5,204,997 | 4/1993 | Suzuki et al. | 604/385.2 |

FOREIGN PATENT DOCUMENTS

| 0309246 | 3/1989 | European Pat. Off. | |
| 3-202057 | 9/1991 | Japan | 604/385.2 |
| 2103093 | 2/1983 | United Kingdom | |
| 2161059 | 1/1986 | United Kingdom | |
| 2216393 | 10/1989 | United Kingdom | |
| 2251172 | 7/1992 | United Kingdom | |
| 9108717 | 6/1991 | World Int. Prop. O. | |
| 9214429 | 9/1992 | World Int. Prop. O. | |

*Primary Examiner*—Randall L. Green
*Assistant Examiner*—Rob Clarke
*Attorney, Agent, or Firm*—Fred Philpitt

[57] ABSTRACT

To prevent a part of excretions having missed an opening formed in a skin-contacting topsheet 14 of a disposable diaper from diffusively flowing over the top surface of this topsheet 14, the opening 16 is provided along the laterally opposite sides thereof with a pair of first flaps 17 opposed to and spaced from each other by a relatively small distance and a pair of second flaps 18 similarly opposed to and spaced from each other by a relatively large distance so that the part of excretions having missed the opening 16 defined by the laterally opposite side edges of the first flaps 17 may be reliably dammed by the second flaps 18 and thereby the diffusive flowing of excretion may be avoided.

3 Claims, 3 Drawing Sheets

DISPOSABLE DIAPERS

BACKGROUND OF THE INVENTION

This invention relates to a disposable diaper used to absorb and hold excretions from human body.

Japanese Utility Model Application Disclosure Gazette No. 1974-120439 discloses a diaper-cover having a topsheet formed at its central zone with an opening extending longer in the longitudinal direction than in the transverse direction of the topsheet, wherein the opening is provided along its peripheral edge with a longitudinally stretchable elastic member so as to define a closed loop-shaped elastic line. Japanese Patent Application Disclosure Gazette No. 1986-41304 also discloses a disposable diaper having a topsheet formed at its central zone with an opening extending longer in the longitudinal direction than in the transverse direction of the topsheet, wherein the opening is provided along its laterally opposite side edges with elastic members, respectively. With these diaper-cover and diaper both having the openings, excretions flow through said opening into pockets defined between said topsheet and a separately provided topsheet underlying a first-mentioned topsheet and is held therein.

Certainly, a flow of excretions will be reliably guided into said opening merely by approximately dimensioning said opening, i.e., in an adequately large size. However, such measure will lead to a corresponding increase of the area over which the above-mentioned separate topsheet underlying the skin-contacting topsheet formed with said opening is exposed and, in consequence, an effect to be provided by said skin-contacting topsheet will unacceptably decrease. Accordingly, said opening must be dimensionally designed in consideration of such problem. Even if the opening is properly designed, however, said opening might be often misaligned with the ideal location in the crotch zone of the diaper wearer depending on a manner in which the helper has put the diaper on the wearer or the wearer moves with the diaper worn on his or her body. In such case, excretions may partially flow and spread over the top of said skin-contacting topsheet and the wearer's skin may be smeared with excretions. The diaper as well as the diaper-cover of well known art as mentioned above can not solve such problem and even a suggestive description about its solution can not found in the above-mentioned publications.

It is a principal object of the invention to provide a disposable diaper so improved that said opening effectively prevent excretion from flowing and spreading over the top of said skin-contacting topsheet even when excretions partially miss the opening.

SUMMARY OF THE INVENTION

The object set forth above is achieved, in accordance with the invention, by a disposable diaper comprising a liquid-permeable first topsheet, a liquid-impermeable backsheet, a liquid absorbent core sandwiched between said first topsheet and said backsheet, and a liquid-resistant second topsheet lying over said first topsheet, wherein said second topsheet is formed substantially at its central zone with an opening extending longer in the longitudinal direction than in the transverse direction of the second topsheet; wherein said second topsheet is bonded along its outer periphery to said first topsheet; and wherein longitudinally stretchable elastic members are attached onto said second topsheet along the peripheral edge of said opening, characterized in that said opening is provided with a pair of first flaps respectively having the first inner side edges opposed to and spaced from each other and a pair of second flaps respectively having the second inner edges opposed to and spaced from each other by a distance larger than the distance by which said first inner side edges are spaced from each other, said pair of second flaps being continuous with the bottom side edges of the respective first flaps; and said second inner side edges are positioned between the first inner side edges and the associated bottom side edges of the respective first flaps so that these second inner side edges may rise up above top surfaces of the respective first flaps and at least said first inner side edges contain therein said elastic members, respectively.

Preferably, said first and second flaps are formed by folding the opposite inner side edges of said opening.

Preferably, said second topsheet comprises a pair of sheet members respectively including said first and second flaps.

Preferably, the inner side edges of said sheet members mutually opposed in the proximities of longitudinally opposite ends thereof are bonded together so that these bonded inner side edges may be separated from each other without any rupture occurring in said sheet members themselves.

With the diaper constructed according to the invention as has been outlined above, said first and second flaps surrounding said opening rise up above said first topsheet as said elastic members contract during actual use of the diaper. In this state of the diaper, substantially all of excretions flow through said opening defined between said first inner edges of the respective first flaps into pockets defined between said first and second topsheets, then solid excretion is held within these pockets while liquid excretion is absorbed through said first topsheet into said absorbent core and held therein. A part of excretions having missed said opening is dammed by said second flaps and thereby this part of excretions is prevented from diffusively flowing over the top surface of said second topsheet.

BRIEF DESCRIPTION OF THE DRAWINGS

The invention will be described by way of example in reference with the accompanying drawings, in which.

PREFERRED EMBODIMENTS OF THE INVENTION

Figure 1:
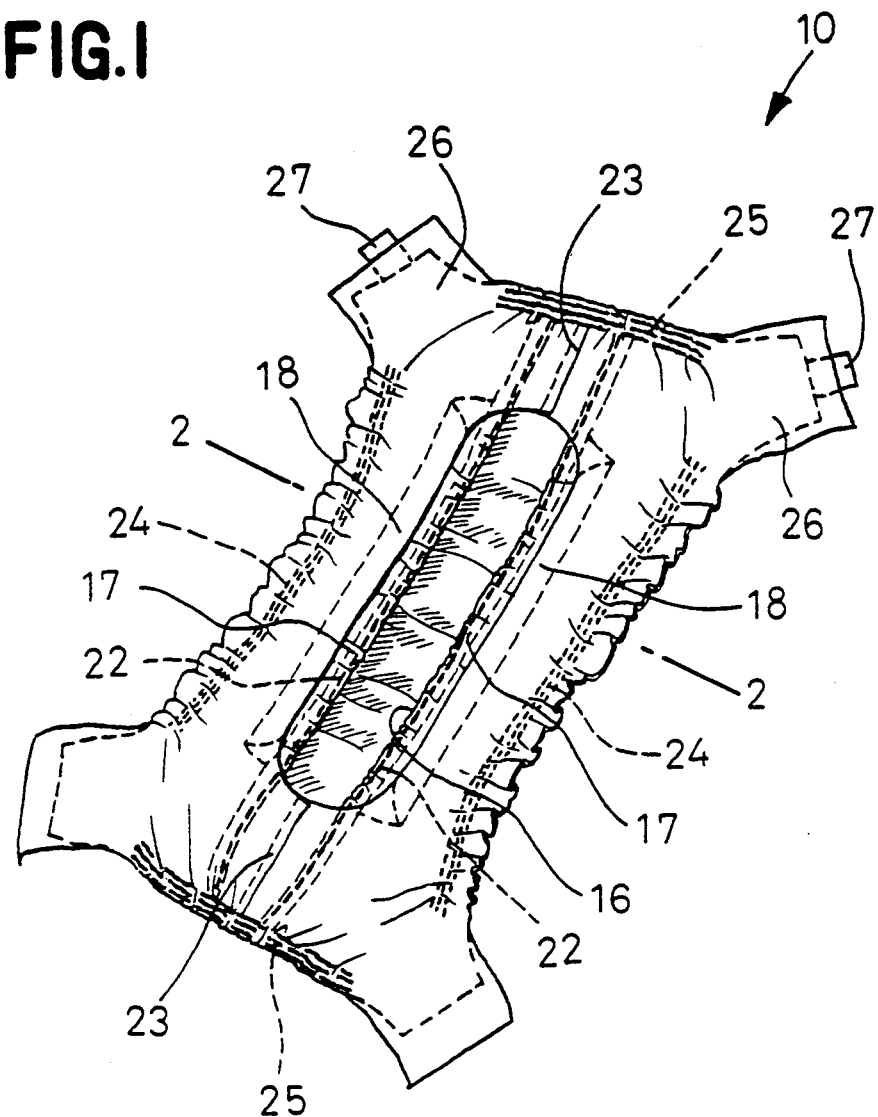
FIG. 1 is a perspective view showing the inner side of a disposable diaper constructed as an embodiment of the invention.
Figure 2:
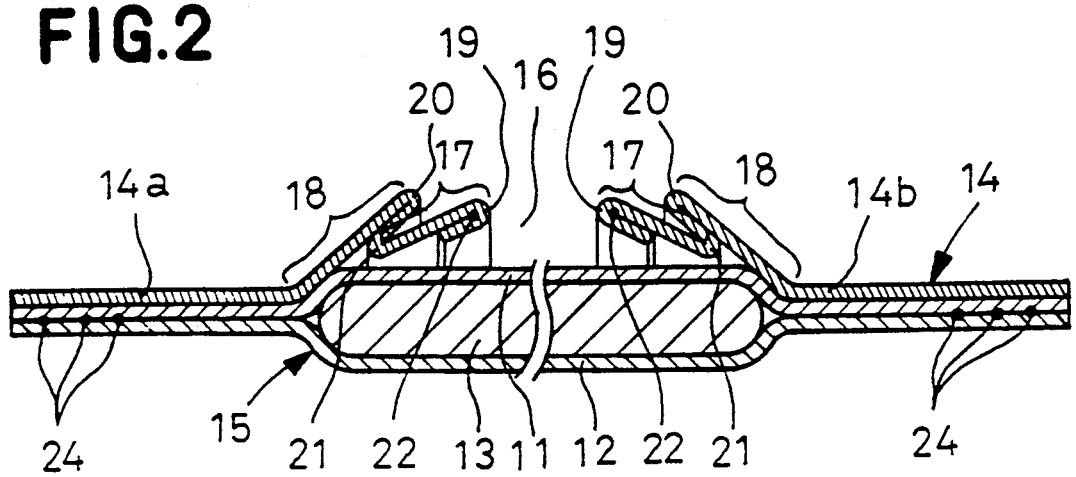
FIG. 2 is a sectional view showing this embodiment, in an enlarged scale, taken along a line 2—2 in FIG. 1.

Referring to FIGS. 1 and 2, a diaper 10 comprises a liquid-permeable first topsheet 11, a liquid-impermeable backsheet 12, a liquid-absorbent core 13 sandwiched therebetween, and a liquid-resistant second topsheet 14. The second topsheet 14 is centrally formed with an opening 16 which is longer in the longitudinal direction than in the transverse direction of this sheet 14 and has longitudinally opposite ends describing circular arcs, respectively. The opening 16 may be formed at least within the crotch zone.

The second topsheet 14 actually comprises a pair of sheet members 14a, 14b. The opening 16 is provided at laterally opposite sides with first and second flaps 17, 18, which are formed by folding the inner portions of the respective sheet members 14a, 14b. More specifically, the inner portions of the respective sheet members 14a, 14b may be downwardly folded to form the second flaps 18, 18 each having a second inner side edge 20, then the portions of the respective sheet members 14a, 14b which inwardly extend from the respective second flaps may be folded upward and thereafter the innermost portions of the respective sheet members 14a, 14b may be downwardly folded to form the first flaps 17, 17 each having a first inner side edge 19. It should be understood that, during formation of each flap, the opposite inner surfaces of each folded portion are bonded together by use of suitable bonding means (e.g., hot melt type adhesive or welding). As will be apparent from such procedure, the second flaps 18, 18 are continuous with bottom side edges 21, 21 of the respective first flaps 17, 17, the second side edges 20, 20 are positioned above the associated first flaps 17, 17 between the first side edges 19, 19 and the bottom side edges 21, 21 thereof, and the opposite second inner side edges 20, 20 are spaced from each other by a distance larger than the distance by which the opposite first inner side edges 19, 19 are spaced from each other. The first inner side edges 19, 19 respectively contain therein longitudinally stretchable elastic members 22, 22 each comprising a single or a plurality of elastic threads mounted therein under their stretched states with use of hot melt type adhesive (not shown). The second inner side edges 20, 20 also may contain therein similar elastic members, respectively, if desired.

Referring to FIG. 1, the opposite inner side edges 23, 23 of the sheet members 14a, 14b which overlap on one another in the proximities of longitudinally opposite ends thereof are bonded to each other in such a manner that the helper for diaper wearing can easily separate them from one another. Specifically, these opposite inner side edges 23, 23 may be either bonded together utilizing hot melt type adhesive or intermittently welded together.

Between the first topsheet 11 and the backsheet 12 both extending outward from the laterally opposite sides of the liquid-absorbent core 13, there are provided adjacent the outer edges of these sheets a plurality of parallelly extending elastic members 24 each comprising, in turn, a plurality of elastic threads attached under their stretched states with use of hot melt type adhesive (not shown), respectively, so as to be stretchable longitudinally of the sheets and thereby to fit tightly around the wearer's legs. Similarly, between the longitudinally opposite ends of the first topsheet 11 and the associated ends of the backsheet 12, there are provided a plurality of elastic members 25 each comprising a plurality of elastic threads, respectively, so as to be stretchable transversely of these sheets and thereby to fit tightly around the wearer's waist.

The first topsheet 11 may be made of nonwoven fabric, porous plastic film or the like, the backsheet 12 may be made of plastic film, laminated sheet of this plastic film and nonwoven fabric or the like, and the liquid-absorbent core 13 may be made of a mixture of fluff pulp and high absorption polymer powder or the like. The second topsheet 14 is preferably made of water-repellent and highly air-permeable nonwoven fabric. It should be understood that, in description of the invention, the "liquid-resistant" material refers to the material having a sufficient degree of water-repellence to prevent liquid excretion from easily penetrating therethrough with the diaper being worn on the wearer's body.

Referring again to FIG. 1, the diaper 10 has two pairs of wing-like flaps 26 extending outward from the laterally opposite sides of the waist line, respectively, and the free ends of tape fasteners 27 attached to the rear side wing-like flaps may be adhesively secured to the backsheet 12 on the front side to erect the diaper 10 around the wearer's body.

Now procedures for formation of said opening 16, said first and second flaps 17, 18 and for attachment of said elastic members 22, 22 will be described in reference with FIGS. 3 through 7.

Figure 3:
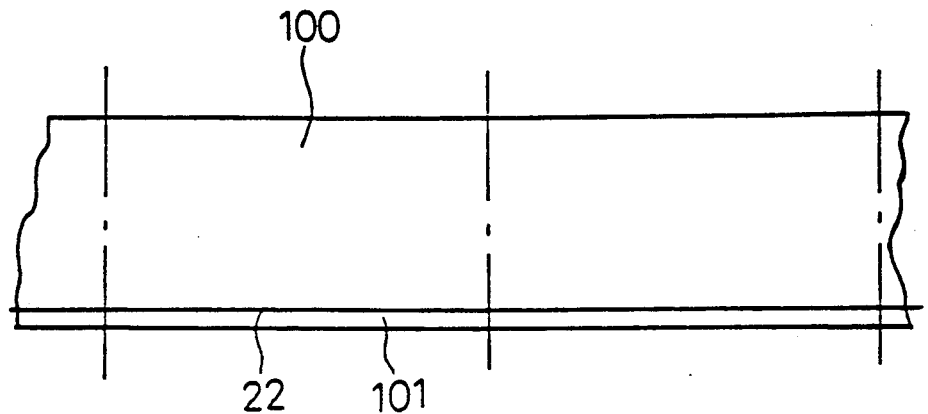
FIG. 3 is a plan view illustrating a manner in which continuous elastic members are attached to a continuous sheet member as the starting material for a second topsheet.

Referring to FIG. 3, a continuous elastic members 22 under elongation at a predetermined percentage are attached to a continuous sheet member 100 (i.e., a continuous web comprising said sheet members 14a, 14b) closely along one side edge extending longitudinally of the sheet with use of hot melt type adhesive (not shown).

Figure 4:
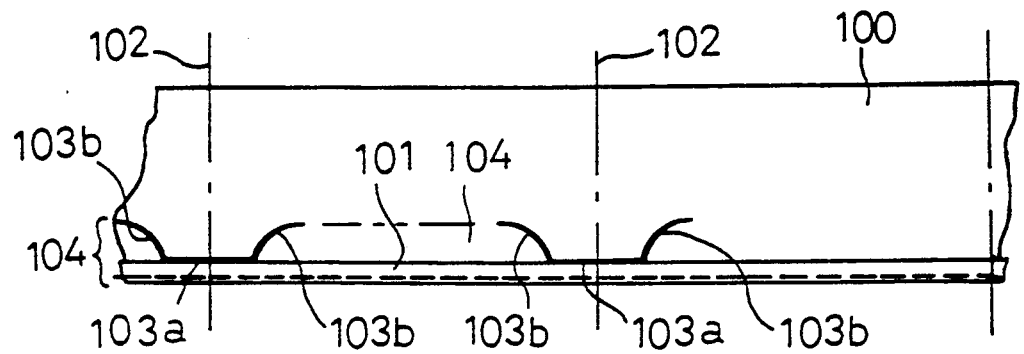
FIG. 4 is a plan view illustrating a manner in which a continuous sheet member is provided with cut lines so that said sheet member may be twice folded back starting from one side edge of said sheet member to form first and second flaps as well as the recess which cooperates with the counter-recess to define an opening.

As will be apparent from FIG. 4, an edge region 101 including said elastic members 22 attached to the sheet is folded back and bonded to the opposed surface with use of hot melt type adhesive or welding. Then, the continuous sheet member 100 is provided with straight cut lines 103a extending along the inner side edge of said edge region 101 across respective lines 102 which extend, in turn, transversely of the continuous sheet member 100, along which lines 102 the continuous sheet member 100 are cut later to define individual diapers. In addition, the continuous sheet member 100 is provided with circular-arc-shaped cut lines 103b extending from the ends of the respective straight cut lines 103a.

Figure 5:
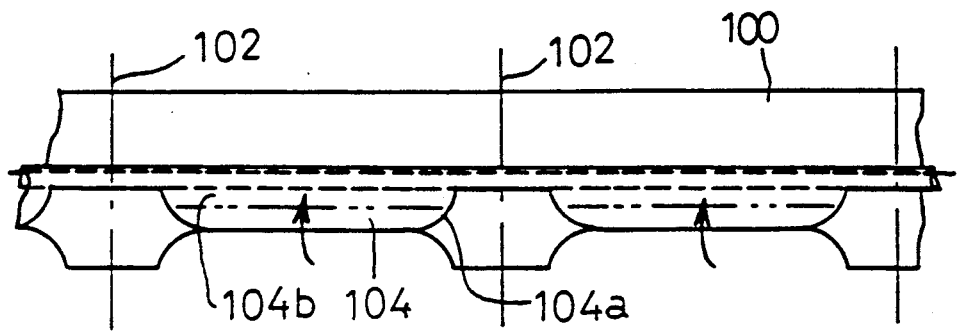
FIG. 5 is a plan view illustrating a manner in which a part of said sheet member is folded inward utilizing said cut lines.

Referring to FIG. 5, each region 104 (to be formed into said first and second flaps 17, 18) defined by the straight and circular-arc-shaped cut lines 103a, 103b, inclusively of the edge region 101, is folded inward along a straight line connecting the inner ends of the circular-arc-shaped cut lines 103b between each pair of the adjacent lines 102.

Figure 6:
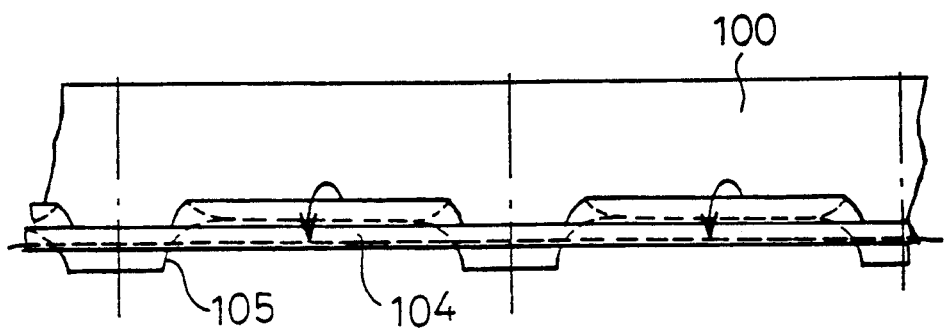
FIG. 6 is a plan view illustrating a manner in which the part of the sheet member having been folded inward is then partially folded outward.

Referring to FIGS. 5 and 6, reference numeral 104a designates a section making a part of the region 104 and reference numeral 104b designates a section (to be formed into the first flap 17) of which the width is approximately one half with respect to said section 104a, and the former section is folded outward.

Figure 7:
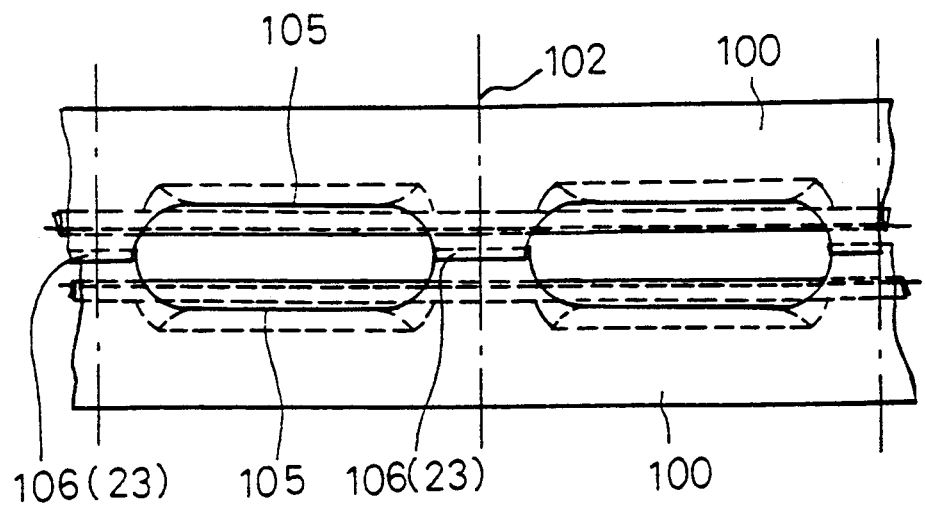
FIG. 7 is a plan view illustrating a manner in which a pair of said sheet members are positioned face to face so that each pair of associated recesses may form the opening.

Referring to FIG. 7, a pair of the sheet members 100 each having recesses 105 defining said openings 16, the first flps 17 containing therein said elastic members 22, and said second flaps 18, are laminated on the top surface of continuous diaper web (not shown) comprising the individual diapers as illustrated by FIGS. 1 and 2 (except for absence of the second topsheet 14) so that each pair of the mutually opposed recesses 105 be aligned with each other to form said opening 16 and each pair of mutually opposed inner side edges 106 (corresponding to said inner side edges 23) overlap each other, then bonded to said diaper web at desired locations with use of hot melt type adhesive or the like and this laminated web is cut along the lines 102 to obtain the individual diapers as illustrated by FIGS. 1 and 2.

While the embodiment has been illustrated and described as so-called open type diaper utilizing the tape fasteners to close the waist line around the wearer's body, the invention will be applicable also to so-called pants type diaper (inclusive of training pants) having a continuous waist line.

The diaper of this invention arranged and operating as has been described hereinabove effectively alleviates apprehension that the wearer's skin might be smeared with a part of excretions which has missed the opening formed in the second topsheet directly contacting the wearer's skin, giving the wearer unpleasant feelings and even causing the wearer to be attacked with skin diseases, because said part of excretions will be reliably dammed by the second flaps and prevented thereby from diffusively flowing over the top surface of the second topsheet.

According to an additional feature of the invention, the second topsheet comprises a pair of sheet members with their inner side edges are bonded together in the proximities of longitudinally opposite ends thereof so that these bonded inner side edges may be separated to expose the first topsheet underlying the second topsheet to that solid excretion held on the first topsheet may be easily scraped off.

What is claimed is:

1. A disposable diaper comprising:
   (a) a liquid-permeable first topsheet (11), a liquid-impermeable backsheet (12), and a liquid-absorbant core (13) sandwiched between said first topsheet (11) and said backsheet (12),
   (b) a liquid-resistant second topsheet (14) overlying a large portion of said first topsheet (11), said second topsheet (14) comprising a pair of adjacent sheet members (14a, 14b) having facing inner sides and spaced apart outer sides,
      (1) the outer side of each sheet member (14a, 14b) being bonded to an outer side of said first topsheet (11),
      (2) a portion of the facing inner sides of said sheet members (14a, 14b) being spaced apart from each other along a central zone of the diaper so as to form an opening (16) that allows access to said underlying first topsheet (11),
      (3) the remaining portions of the facing inner sides of said sheet members (14a, 14b) being separably adhered to each other along longitudinal lines (23) extending outwardly from both ends of said opening (16),
      (4) each sheet member (14a, 14b) consisting of a single continuous sheet of material that extends from an outer side of said diaper inwardly toward said opening (16) and in the area adjacent said opening (16) forms a single flap member extending above from said first topsheet (11), each flap member comprising a first flap section (17) located closest to the center of said opening (16) and a second flap section (18) located immediately adjacent said first flap section (17) and laterally outwardly therefrom, each first flap section (17) being only attached to a portion of each adjacent second flap section (18) and being unattached to said first topsheet (11), said flap members forming a pocket which extends under said flap members and above said first topsheet (11).

2. A diaper according to claim 1 wherein said remaining portions of the facing inner sides of said sheet members (14a, 14b) are adhered together along a longitudinal line in such a manner that they may be separated from each other without any rupture occurring in said sheet members (14a, 14b).

3. A diaper according to claim 1 wherein said first and second flap sections (17, 18) consist of folded over portions of the inner side portions of said sheet members (14a, 14b).

* * * * *